(12) United States Patent
Genta et al.

(10) Patent No.: US 9,102,956 B2
(45) Date of Patent: Aug. 11, 2015

(54) BIOMASS HYDROTHERMAL DECOMPOSITION APPARATUS, TEMPERATURE CONTROL METHOD THEREOF, AND ORGANIC RAW MATERIAL PRODUCTION SYSTEM USING BIOMASS MATERIAL

(75) Inventors: Minoru Genta, Tokyo (JP); Ryosuke Uehara, Tokyo (JP); Hideo Suzuki, Tokyo (JP); Seiichi Terakura, Tokyo (JP)

(73) Assignee: MITSUBISHI HEAVY INDUSTRIES MECHATRONICS SYSTEMS, LTD., Kobe (JP)

( * ) Notice: Subject to any disclaimer, the term of this patent is extended or adjusted under 35 U.S.C. 154(b) by 1018 days.

(21) Appl. No.: 13/132,040

(22) PCT Filed: Mar. 10, 2010

(86) PCT No.: PCT/JP2010/054023
§ 371 (c)(1),
(2), (4) Date: May 31, 2011

(87) PCT Pub. No.: WO2011/111190
PCT Pub. Date: Sep. 15, 2011

(65) Prior Publication Data
US 2012/0021503 A1 Jan. 26, 2012

(51) Int. Cl.
*C12M 1/40* (2006.01)
*B01J 19/00* (2006.01)
*C08B 15/00* (2006.01)
*C12P 7/10* (2006.01)
*C10L 1/02* (2006.01)

(52) U.S. Cl.
CPC ... *C12P 7/10* (2013.01); *C10L 1/02* (2013.01); *C10G 2300/1014* (2013.01); *C10G 2300/805* (2013.01); *Y02E 50/16* (2013.01)

(58) Field of Classification Search
None
See application file for complete search history.

(56) References Cited

U.S. PATENT DOCUMENTS

| 3,985,728 A | 10/1976 | Lin |
| 4,152,197 A | 5/1979 | Lindahl et al. |

(Continued)

FOREIGN PATENT DOCUMENTS

| CA | 2660990 A1 | 8/2009 |
| CA | 2666152 A1 | 4/2010 |

(Continued)

OTHER PUBLICATIONS

U.S. Non-Final Office Action dated Dec. 17, 2013, issued in U.S. Appl. No. 13/203,929 (23 pages).

(Continued)

*Primary Examiner* — Melvin C Mayes
*Assistant Examiner* — Douglas Call
(74) *Attorney, Agent, or Firm* — Westerman, Hattori, Daniels & Adrian, LLP

(57) ABSTRACT

A biomass hydrothermal decomposition apparatus that feeds a solid biomass material 11 from one side of an apparatus body 42, feeds hot water 15 from the other side, to hydrothermally decompose the biomass material 11 while bringing the biomass material 11 into counter contact with the hot water 15, dissolves hot-water soluble fractions in hot water, discharges the hot water to outside from the one side of the apparatus body 42 as a hot-water effluent 16, and discharges a biomass solid (a hot water insoluble) 17 to outside from the other side. The biomass hydrothermal decomposition apparatus includes an effective reaction region A formed from the other side to the one side of the apparatus body 42, in which a feeding temperature of the hot water 15 (for example, 200° C.) is maintained for a predetermined period of time to cause hydrothermal decomposition, and a temperature drop region B in which a temperature is rapidly dropped to a temperature (for example, 140° C.) at which the hot-water soluble fractions are not excessively decomposed (for example, from 200° C. to 140° C.), immediately after it is out of the effective reaction region A.

1 Claim, 10 Drawing Sheets

(56) References Cited

U.S. PATENT DOCUMENTS

| | | | | |
|---|---|---|---|---|
| 4,746,401 | A | * | 5/1988 | Roberts et al. ............... 162/72 |
| 4,859,322 | A | | 8/1989 | Huber |
| 5,348,871 | A | | 9/1994 | Scott et al. |
| 5,411,594 | A | | 5/1995 | Brelsford |
| 5,424,417 | A | | 6/1995 | Torget et al. |
| 5,466,108 | A | | 11/1995 | Piroska |
| 6,022,419 | A | | 2/2000 | Torget et al. |
| 6,419,788 | B1 | * | 7/2002 | Wingerson ............... 162/14 |
| 8,123,864 | B2 | | 2/2012 | Christensen et al. |
| 8,163,517 | B2 | | 4/2012 | Genta et al. |
| 2007/0231869 | A1 | | 10/2007 | Holmgren et al. |
| 2007/0259412 | A1 | | 11/2007 | Belanger et al. |
| 2008/0032344 | A1 | | 2/2008 | Fallavollita |
| 2008/0044891 | A1 | | 2/2008 | Kinley et al. |
| 2008/0299628 | A1 | | 12/2008 | Hallberg et al. |
| 2010/0108567 | A1 | | 5/2010 | Medoff |
| 2010/0184176 | A1 | | 7/2010 | Ishida et al. |
| 2010/0269990 | A1 | | 10/2010 | Dottori et al. |
| 2010/0285574 | A1 | | 11/2010 | Genta et al. |
| 2010/0330638 | A1 | | 12/2010 | Aita et al. |
| 2011/0079219 | A1 | | 4/2011 | McDonald et al. |
| 2011/0314726 | A1 | | 12/2011 | Jameel et al. |
| 2012/0006320 | A1 | | 1/2012 | Nguyen |
| 2012/0315683 | A1 | | 12/2012 | Mosier et al. |
| 2014/0004571 | A1 | | 1/2014 | Garrett et al. |
| 2014/0273127 | A1 | | 9/2014 | Fuchs et al. |

FOREIGN PATENT DOCUMENTS

| | | |
|---|---|---|
| CA | 2654306 C | 10/2013 |
| EP | 0 098 490 A2 | 1/1984 |
| JP | 9-507386 A | 7/1997 |
| JP | 11-506934 T | 6/1999 |
| JP | 2001-170601 A | 6/2001 |
| JP | 2002-059118 A | 2/2002 |
| JP | 2003-311141 A | 11/2003 |
| JP | 2004-105855 A | 4/2004 |
| JP | 2005-27541 A | 2/2005 |
| JP | 2005-168335 A | 6/2005 |
| JP | 2005-205252 A | 8/2005 |
| JP | 2005-229821 A | 9/2005 |
| JP | 2006-036977 A | 2/2006 |
| JP | 2006-68399 A | 3/2006 |
| JP | 2006-136263 A | 6/2006 |
| JP | 2006-223152 A | 8/2006 |
| JP | 2006-289164 A | 10/2006 |
| JP | 2007-112880 A | 5/2007 |
| JP | 2007-202560 A | 8/2007 |
| JP | 2007-301472 A | 11/2007 |
| JP | 2008-054608 A | 3/2008 |
| JP | 2008-104452 A | 5/2008 |
| JP | 2008-278825 A | 11/2008 |
| JP | 2009-183153 A | 8/2009 |
| JP | 2009-183154 A | 8/2009 |
| JP | 2009-183805 A | 8/2009 |
| JP | 2010-17084 A | 1/2010 |
| JP | 4764527 B1 | 9/2011 |
| JP | 4764528 B1 | 9/2011 |
| WO | 84/03304 A1 | 8/1984 |
| WO | 95/17517 A1 | 6/1995 |
| WO | 96/40970 A1 | 12/1996 |
| WO | 2009/096060 A1 | 8/2009 |
| WO | 2009/096062 A1 | 8/2009 |
| WO | 2009/124240 A1 | 10/2009 |
| WO | 2010/038302 A1 | 4/2010 |

OTHER PUBLICATIONS

U.S. Non-Final Office Action dated Dec. 16, 2013, issued in U.S. Appl. No. 13/132,034 (29 pages).
Gregg, D. et al., "Bioconversion of Lignocellulosic Residue to Ethanol: Process Flowsheet Development", Biomass and Bioenergy, 1995, vol. 9, No. 1-5, pp. 287-302, Cited in U.S. Office Action dated Dec. 17, 2013.
Canadian Office Action dated Nov. 8, 2013, issued in Canadian Patent Application No. 2,801,383 (2 pages).
Indonesian Notice of Allowance dated Nov. 15, 2013, issued in Indonesian Patent Application No. W-00201002623, w/English translation, (5 pages).
U.S. Non-Final Office Action dated Jan. 30, 2014 issued in U.S. Appl. No. 12/438,792 (39 pages).
Canadian Notice of Allowance dated Jan. 13, 2014, issued in Canadian Patent Application No. 2,744,522 (1 page).
U.S. Non-Final Office Action dated Jan. 30, 2014, issued in U.S. Appl. No. 13/578,116 (22 pages).
Written Opinion of PCT/JP2010/054023, mailed on Jun. 15, 2010.
Office Action of Application No. 2010-536272, mailed on Nov. 9, 2010.
International Search Report of PCT/JP2010/054023, mailed on Jun. 15, 2010.
Genta, "NEDO ni yoru Biomass Energy to Ko Koritsu Tenkan Gijutsu Kaihatsu 1), Suinetsu Bunkaiho to Koso Bunkaiho wo Kumiawaseta Nogyo Zansa to no Cellulose-kei Biomass no Tei Cost Toka Gijutsu no Kaihatsu" Clean Energy, 2010, pp. 11-15, cited in the Australian Notice of Acceptance dated Mar. 17, 2014.
Canadian Office Action dated Mar. 31, 2014, issued in Canadian Patent Application No. 2,750,753 (3 pages) (corresponding to U.S. Appl. No. 13/203,929).
U.S. Final Office Action dated May 22, 2014, issued in U.S. Appl. No. 13/700,753 (40 pages).
U.S. Final Office Action dated Jun. 3, 2014, issued in U.S. Appl. No. 13/203,929 (22 pages).
Arroyo-Lopez, F.N. et al., "Effects of temperature, pH and sugar concentration on the growth parameters of *Saccharomyces cerevisiae*, *S. kudriavzevii* and their interspecific hybrid", International Journal of Food Microbiology, vol. 131, pp. 120-127 (2009).
Turton, L.J. et al., "Effect of Glucose Concentration in the Growth Medium Upon Neutral and Acidic Fermentation End-products of *Clostridium bifermentans, Clostridium sporogenes* and *Peptostreptococcus anaerobius*", J. Med. Microbiol., vol. 16, pp. 61-67 (1983).
Dien, B.S. et al., "Fermentation of hexose and pentose sugars using a novel ethanologenic *Escherichia coli* strain", Enzyme and Microbial Technology, vol. 23, pp. 366-371 (1998).
U.S. Office Action dated Aug. 19, 2013, issued in U.S. Appl. No. 13/578,116.
U.S. Office Action dated Oct. 3, 2013, issued in U.S. Appl. No. 13/782,545.
English translation of JP 2009-183805 previously filed on Mar. 31, 2011, cited in U.S. Office Action U.S. Appl. No. 13/782,545.
Notice of Allowance dated Nov. 9, 2012, issued in corresponding Canadian Patent Application No. 2,741,598 (1 page).
Kunagai, Satoshi et al.; "Fractionation and Saccharification of Cellulose and Hemicellulose in Rice Hull by Hot-Compressed-Water Treatment with Two-Step Heating", Journal of the Japan Institute of Energy, Dec. 1, 2003, vol. 83, pp. 776-781.(partial English translation).
Nikkei Biotechnology & Business, "Biomass Ethanol"; Nikkei Business Publications Inc. (Nikkei Biotechnology & Business Sep. 2002). (partial English translation).
Written Opinion of the International Searching Authority dated Jun. 15, 2010, issued in International Application No. PCT/JP2010/054023. (partial English translation).
Canadian Notice of Allowance dated Aug. 22, 2013, issued in Canadian Patent Application No. 2666152.
Canadian Notice of Allowance dated Aug. 22, 2013, issued in Canadian Patent Application No. 2713529.
U.S. Office Action dated Oct. 28, 2013, issued in U.S. Appl. No. 12/443,515.
U.S. Office Action dated Oct. 7, 2013, issued in U.S. Appl. No. 13/700,753.
U.S. Restriction/Election dated Aug. 22, 2013, issued in U.S. Appl. No. 13/700,753.
US Final Office Action dated Feb. 13, 2014, issued in U.S. Appl. No. 12/865,273 (26 pages).
Liu, Chaogang, et al., "Continuous Fermentation of Hemicellulose Sugars and Cellulose to Ethanol", International Symposia on Alcohol

(56) References Cited

OTHER PUBLICATIONS

Fuels, (2005), pp. 1-28 (cited in U.S. Final Office Action dated Feb. 13, 2014, issued in U.S. Appl. No. 12/865,273).
U.S. Non-Final Office Action issued Mar. 10, 2014, in related U.S. Appl. No. 13/782,545 (27 pages).
Decision of a Patent Grant dated Mar. 4, 2014, issued in JP2009-252201 (corresponding to U.S. Appl. No. 12/443,515), w/English translation (4 pages).
Decision of a Patent Grant dated Mar. 4, 2014, issued in JP2009-245963 (corresponding to U.S. Appl. No. 12/438,792) w/English translation (4 pages).
Australian Notice of Acceptance dated Mar. 17, 2014, issued in Australian patent application No. 2011355013 (corresponding to U.S. Appl. No. 13/578,116) (2 pages).
U.S. Office Action dated Apr. 14, 2014, issued in U.S. Appl. No. 12/443,515 (16 pages).
U.S. Final Office Action dated Jul. 3, 2014, issued in U.S. Appl. No. 13/578,116 (17 pages).
U.S. Final Office Action dated Aug. 18, 2014, issued in U.S. Appl. No. 13/132,034 (30 pages).
U.S. Final Office Action dated Jun. 13, 2014, issued in U.S. Appl. No. 12/438,792 (26 pages).
U.S. Final Office Action dated Jul. 22, 2014, issued in U.S. Appl. No. 12/443,515 (13 pages).
Office Action dated Nov. 14, 2014, issued in Indonesian Patent Application No. W00201102352, (corresponds to U.S. Appl. No. 13/121,969), w/English translation.
Office Action dated Nov. 7, 2014, issued in Indonesian Patent Application No. W00200902414, (corresponds to U.S. Appl. No. 12/434,792), w/English translation.
Genta, M. et al., "Suinetsu Bunkaiho to Koso Bunkaiho o Kumiawaseta Nogyo Zansa To no Cellulose Biomass no Tei Cost Toka Gijutsu no Kaihatsu", Heisei 21 Nendo Biomass Energy Kanren Jigyo Seika Hokokukai, Feb. 11, 2010, pp. 55-69, URL, http://www.nedo.go.jp/events/report/FF__00003.html, Cited in JP Office Action dated Oct. 14, 2014.
Lehrburger, E. "Developing biorefineries to produce energy, ethanol and other industrial products", PureVision Technology, Inc., Alternative Energy Conference, Mar. 3, 2005, pp. 1-26, Cited in U.S. Office Action dated Nov. 6, 2014.
U.S. Office Action dated Sep. 30, 2014, issued in U.S. Appl. No. 13/782,545 (43 pages).
U.S. Office Action dated Nov. 6, 2014, issued in U.S. Appl. No. 12/865,273 (27 pages).
Japanese Office Action dated Oct. 14, 2014, issued in Japanese Patent Application No. 2010-154233 (corresponds to U.S. Appl. No. 13/700,753), with English Translation (7 pages).
U.S. Office Action dated Dec. 5, 2014, issued in U.S. Appl. No. 13/121,969.
Canadian Notice of Allowance dated Dec. 5, 2014, issued in Canadian Patent Application No. 2750754 (corresponds to U.S. Appl. No. 13/203,848).
Indonesian Office Action dated Oct. 29, 2014, issued in Indonesian Patent Application No. W00201103522 (corresponds to U.S. Appl. No. 13/203,929), w/English translation.
U.S. Notice of Allowance dated Nov. 5, 2014, issued in U.S. Appl. No. 12/443,515.
International Search Report dated Jul. 3, 2012 issued in International Application No. PCT/JP2012/058460 (corresponds to U.S. Appl. No. 14/381,511).
Written Opinion of the International Searching Authority dated Jul. 3, 2012 issued in International Application No. PCT/JP2012/058460 (corresponds to U.S. Appl. No. 14/381,511).
Decision of a Patent Grant dated Nov. 12, 2013, issued in Japanese Patent Application No. 2013-536355, w/ English translation (corresponds to U.S. Appl. No. 14/381,511) (4 pages).
U.S. Office Action dated Apr. 24, 2015, issued in U.S. Appl. No. 14/381,511 (20 pages).
Notice of Allowance and Fee(s) Due dated Feb. 17, 2015, issued in U.S. Appl. No. 13/782,545 (20 pages).
U.S. Office Action dated Mar. 19, 2015, issued in U.S. Appl. No. 13/121,969 (21 pages).
U.S. Office Action dated Mar. 13, 2015, issued in U.S. Appl. No. 13/722,385 (41 pages).
U.S. Office Action dated Mar. 31, 2015, issued in U.S. Appl. No. 12/865,273 (25 pages).
U.S. Office Action dated May 13, 2015, issued in U.S. Appl. No. 12/438,792 (11 pages).
Non-Final Office Action dated Jun. 19, 2015, issued in related U.S. Appl. No. 13/700,753 (11 pages).

* cited by examiner

XYLOSE REDUCTION RATE IN HOT WATER SOLUBLE

BIOMASS HYDROTHERMAL DECOMPOSITION APPARATUS, TEMPERATURE CONTROL METHOD THEREOF, AND ORGANIC RAW MATERIAL PRODUCTION SYSTEM USING BIOMASS MATERIAL

FIELD

The present invention relates to a biomass hydrothermal decomposition apparatus that can hydrothermally decompose a biomass material efficiently, a temperature control method thereof, and an organic raw material production system that uses a biomass material and can efficiently produce an organic raw material such as alcohol, substitutes for petroleum, or amino acid, the production system using the biomass hydrothermal decomposition apparatus and the method thereof.

BACKGROUND

Conventionally, a technique for producing ethanol or the like, in which solid-liquid separation is performed after saccharification of biomass such as wood by using diluted sulfuric acid or concentrated sulfuric acid, and a liquid phase is neutralized and used as a raw material for ethanol fermentation, has been practical utilized (Patent Literature 1, Patent Literature 2).

Further, production of chemical industrial raw materials (for example, lactic acid fermentation) using sugar as a starting material can be also considered.

In this specification, "biomass" represents organisms incorporated in a substance circulatory system of the global biosphere or accumulation of organic matters derived from the organisms (see JIS K 3600 1258).

Sugarcane, corn and the like, which are currently used as alcohol raw materials, are originally used as food and using these edible resources as industrial resources in a long term and in a stable manner is not preferable in view of a life cycle of effective foodstuff.

Therefore, it is an important issue to effectively use cellulose resources such as herbal biomass and wood-based biomass, which are believed to be useful industrial recourses in the future.

Further, in the cellulose resources, the resource component ratio is varied such that the ratio of cellulose is 38% to 50%, that of hemicellulose component is 23% to 32%, and that of lignin component, which is not used as a fermentation raw material, is 15% to 22%. Because industrial researches have been conducted with many unsolved problems, raw materials in the researches are assumed in a fixed manner, and currently there is no disclosure of a technique of a production system with taking the material versatility of into consideration.

Originally, because issues of waste and prevention of the global warming are taken into consideration according to a method unfavorable to fermentation feedstock as compared with starch feedstock, there is less point in the production system in which raw materials are considered in a fixed manner. This production system should be widely applicable to general waste materials. Enzymic saccharification itself is not efficient at all, and is thought to be an issue that should be solved in the future. A saccharification rate by acid treatment has a considerably small value of about 75% (on a component basis capable of being saccharified) due to excessive decomposition of sugar caused by overreaction. Therefore, the production yield of ethanol is about 25% with respect to the cellulose resources (Patent Literature 1, Patent Literature 3).

In the conventional techniques disclosed in Patent Literatures 1 to 3, there has been a phenomenon in which a reaction by-product causes inhibition of enzymic saccharification to decrease the sugar yield. Therefore, a hydrothermal decomposition apparatus that removes a substance inhibiting enzymic saccharification to increase activity of enzyme based on cellulose has been proposed (Patent Literatures 4 and 5).

CITATION LIST

Patent Literatures

Patent Literature 1: Japanese Patent Application National Publication No. H9-507386
Patent Literature 2: Japanese Patent Application National Publication No. H11-506934
Patent Literature 3: Japanese Patent Application Laid-open No. 2005-168335
Patent Literature 4: Japanese Patent Application Laid-open No. 2009-183805
Patent Literature 5: Japanese Patent Application Laid-open No. 2009-183154

Non Patent Literature

Non Patent Literature 1: Nikkei Bio Business, p. 52, September 2002

SUMMARY

Technical Problem

In the hydrothermal decomposition apparatus according to Patent Literatures 4 and 5 mentioned above, biomass and pressurized hot water are fed into counter contact with each other to cause hydrothermal reaction by internal heat exchange. However, a temperature distribution occurs at an internal temperature.

FIG. 10 is a pattern diagram of a vertical apparatus according to a conventional example that hydrothermally decomposes biomass by hot water.

As shown in FIG. 10, in this vertical hydrothermal decomposition apparatus, biomass (solid) 11 is fed into an apparatus body 42 from a bottom side and moved to an upper side by a transfer screw 43 provided therein, and a biomass solid (a hot water insoluble) 17 is discharged to outside from the upper side.

On the other hand, pressurized hot water (hereinafter, also "hot water") 15 is fed into the apparatus body 42 from the upper side and brought into counter contact with the biomass 11, and a hot-water effluent 16 is discharged to the outside from the bottom side. Therefore, in the apparatus body 42, the temperature is dropped gradually from a side for feeding the hot water 15 (upper side) toward the bottom side (a side for feeding biomass).

FIG. 11 depicts a decomposition state of biomass by hot water.

As shown in FIG. 11, biomass (cellulostic raw material) includes hemicellulose and lignin other than cellulose. Specifically, the biomass has a structure such that cellulose is bundled by the hemicellulose, and lignin is bonded thereto.

After hydrothermal decomposition, biomass is divided into a hot water insoluble (a solid) and a hot water soluble.

Therefore, the biomass material 11 is hydrothermally decomposed in a high temperature range (180° C. to 240° C.) by the hot water 15, and hemicellulose is dissolved and lignin is also decomposed and dissolved on the hot water side. As a result, hemicellulose and the like are dissolved on the hot water side.

In a state of hot-water solubilized hemicellulose after being solubilized in hot water, there is a problem that excessive decomposition occurs in the high temperature range (180° C. to 240° C.).

That is, when all of the hemicellulose is solubilized immediately after the biomass material 11 is input into the apparatus body and brought into contact with the hot water 15, the solubilized hemicellulose is immediately discharged to outside as the hot-water effluent 16 due to the effect of counter contact. Therefore, the excessive decomposition time is short. However, when the biomass material is raised in the hot water 15, and the hemicellulose is solubilized near a position where the biomass material is discharged as the biomass solid 17, the solubed hemicellulose is brought into contact with high-temperature hot water for a long time until the solubed hemicellulose is discharged from the bottom side of the apparatus as the hot-water effluent 16. Therefore, excessive decomposition proceeds, and this causes another problem.

This excessive decomposition of hemicellulose decreases the yield of hemicellulose, which becomes a raw material of C5 sugar, and thus it is desired to suppress the excessive decomposition of hemicellulose into a hot water soluble, thereby improving plant operation efficiencies.

Further, mixing of an excessive decomposition product into hot water inhibits fermentation of C5 sugar and alcohol in the facilities on the downstream side. Therefore, it is required to prevent generation of the inhibitor.

The present invention has been achieved in view of the above problems, and an object of the present invention is to provide a biomass hydrothermal decomposition apparatus that can suppress excessive decomposition of hemicellulose as a hot water soluble, in biomass hydrothermal decomposition processing that can separate a component mainly including cellulose from a biomass material, a temperature control method, and an organic raw material production system using a biomass material.

Solution to Problem

According to an aspect of the present invention, biomass hydrothermal decomposition apparatus that feeds a solid biomass material from one side of an apparatus body, feeds hot water from the other side, to hydrothermally decompose the biomass material while bringing the biomass material into counter contact with the hot water in the apparatus body, dissolves hot-water soluble fractions in hot water, discharges the hot water to outside from the one side of the apparatus body, and discharges the biomass material to outside from the other side, includes: an effective reaction region formed from the other side to the one side of the apparatus body, in which a feeding temperature of the hot water is maintained for a predetermined period of time to cause hydrothermal decomposition; and a temperature drop region in which a temperature is rapidly dropped to a temperature at which hot-water soluble fractions are not excessively decomposed, immediately after it is out the effective reaction region.

Advantageously, in the biomass hydrothermal decomposition apparatus, a feeding temperature of the hot water is a predetermined temperature from 180° C. to 240° C., a temperature at which the hot-water soluble fractions are not excessively decomposed is 140° C. or less, and the temperature drop region is a temperature range in which a temperature is dropped from a temperature for feeding the hot water to 140° C. or less.

Advantageously, in the biomass hydrothermal decomposition apparatus, the temperature drop region includes at least two regions.

Advantageously, in the biomass hydrothermal decomposition apparatus, a feeding temperature of the hot water is a predetermined temperature from 180° C. to 240° C., a temperature at which the hot-water soluble fractions are not excessively decomposed is 140° C. or less, a first temperature drop region is a temperature range in which the temperature is dropped from the temperature for feeding the hot water to 180° C., and a second temperature drop region is a temperature range in which the temperature is dropped from 180° C. to 140° C.

Advantageously, in the biomass hydrothermal decomposition apparatus, the hydrothermal decomposition apparatus is a gradient-type or vertical-type apparatus.

According to another aspect of the present invention, an organic raw material production system using a biomass material, includes: a pre-processing apparatus that pre-processes a biomass material; any one of the biomass hydrothermal decomposition apparatus described above; a first enzymatic decomposition device that processes, with an enzyme, cellulose in a biomass solid discharged from the biomass hydrothermal decomposition apparatus to decompose cellulose into a sugar solution containing hexose with the enzyme; and a first fermentation device that produces any one of alcohol, substitutes for petroleum, and amino acid by fermentative treatment, by using a first sugar solution obtained by the first enzymatic decomposition device.

Advantageously, the organic raw material production system using a biomass material, includes: a second enzymatic decomposition device that processes, with an enzyme, hemicellulose in a hot-water effluent to decompose hemicellulose into a sugar solution containing pentose with the enzyme; and a second fermentation device that produces any one of alcohol, substitutes for petroleum, and amino acid by fermentative treatment, by using a second sugar solution obtained by the second enzymatic decomposition device.

Advantageously, the organic raw material production system using a biomass material, includes: a sulfuric-acid decomposition device that decomposes, with sulfuric acid, a hemicellulose component in a hot-water effluent discharged from the hydrothermal decomposition apparatus to decompose the hemicellulose component into a second sugar solution containing pentose; and a second fermentation device that produces any one of alcohol, substitutes for petroleum, and amino acid by fermentative treatment, by using a second sugar solution obtained by the sulfuric-acid decomposition device.

According to still another aspect of the present invention, a temperature control method of a biomass hydrothermal decomposition apparatus includes: using a biomass hydrothermal decomposition apparatus that feeds a solid biomass material from one side of an apparatus body; feeding hot water from the other side, to hydrothermally decompose the biomass material while bringing the biomass material into counter contact with the hot water; dissolving hot-water soluble fractions in hot water; discharging the hot water to outside from the one side of the apparatus body; discharging the biomass material to outside from the other side; performing temperature control in an effective reaction region formed from the other side to the one side of the apparatus body, in which a feeding temperature of the hot water is maintained for a predetermined period of time to cause hydrothermal decomposition; and performing temperature control in a temperature drop region in which a temperature is rapidly dropped to a temperature at which hot-water soluble fractions are not excessively decomposed, immediately after it is out of the effective reaction region.

Advantageously, in the temperature control method of a biomass hydrothermal decomposition apparatus, a feeding temperature of the hot water is a predetermined temperature from 180° C. to 240° C., a temperature at which the hot-water soluble fractions are not excessively decomposed is 140° C. or less, and the temperature drop region is a temperature range in which a temperature is dropped from a temperature for feeding the hot water to 140° C. or less.

Advantageously, in the temperature control method of a biomass hydrothermal decomposition apparatus, the temperature drop region includes at least two regions.

Advantageously, in the temperature control method of a biomass hydrothermal decomposition apparatus, a feeding temperature of the hot water is a predetermined temperature from 180° C. to 240° C., a temperature at which the hot-water soluble fractions are not excessively decomposed is 140° C. or less, a first temperature drop region is a temperature range in which the temperature is dropped from the temperature for feeding the hot water to 180° C., and a second temperature drop region is a temperature range in which the temperature is dropped from 180° C. to 140° C.

Advantageous Effects of Invention

According to the present invention, to maintain hydrothermal decomposition reaction of biomass at a predetermined temperature for a predetermined time by feeding hot water to cause efficient hydrothermal decomposition, and suppress excessive decomposition of hot-water solubilized hemicellulose, which has become a solubilized fraction, by hydrothermal decomposition, a range in which the temperature is rapidly dropped from a hydrothermal decomposition temperature to a temperature at which excessive decomposition does not proceed is provided, thereby enabling to considerably suppress excessive decomposition of hemicellulose. As a result, excessive decomposition of hot-water solubilized hemicellulose is suppressed, and thus a decrease in the yield of C5 sugar can be suppressed.

DESCRIPTION OF EMBODIMENTS

Exemplary embodiments of the present invention will be explained below in detail with reference to the accompanying drawings. The present invention is not limited to the embodiments. In addition, constituent elements in the following embodiments include those that can be easily assumed by persons skilled in the art or that are substantially equivalent.

First Embodiment

A biomass hydrothermal decomposition apparatus according to an embodiment of the present invention is explained with reference to the drawings.

Figure 1:
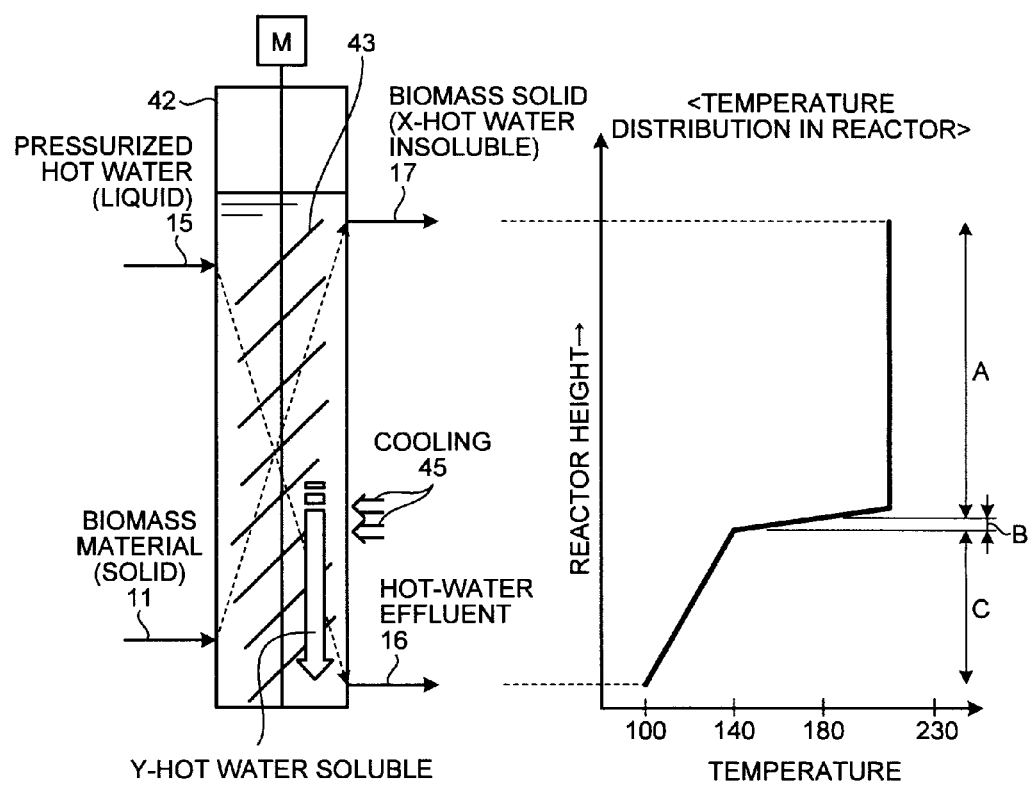
FIG. 1 is a pattern diagram of a hydrothermal decomposition apparatus according to a first embodiment of the present invention and a temperature distribution.

FIG. 1 is a conceptual diagram of a biomass hydrothermal decomposition apparatus according to a first embodiment and a temperature distribution.

As shown in FIG. 1, the biomass hydrothermal decomposition apparatus according to the present embodiment feeds the solid biomass material 11 from one side of the apparatus body 42 by the transfer screw 43, and feeds the hot water 15 from the other side, to hydrothermally decompose the biomass material 11 while bringing the biomass material 11 into counter contact with the hot water 15 in the apparatus body 42. Further, the biomass hydrothermal decomposition apparatus dissolves hot-water soluble fractions (hemicellulose components) in hot water, discharges the hot water to outside from one side of the apparatus body 42 as the hot-water effluent 16, and discharges the biomass solid (a hot water insoluble) 17 to the outside from the other side. The biomass hydrothermal decomposition apparatus includes an effective reaction region (a hydrothermal decomposition region) A formed from the other side to the one side of the apparatus body 42 of the biomass hydrothermal decomposition apparatus, in which the feeding temperature of the hot water 15 (180 to 240° C., such as 200° C.) is maintained for a certain period of time to cause hydrothermal decomposition. The biomass hydrothermal decomposition apparatus further includes a temperature drop region (a dissolved-hemicellulose excessive decomposition suppressing region) B in which the temperature is rapidly dropped (for example, from 200° C. to 140° C.) to a temperature (for example, 140° C.) at which the hot-water soluble fractions are not excessively decomposed, immediately after it is out of the effective reaction region A.

In the present invention, to maintain hydrothermal decomposition reaction of biomass at a predetermined temperature (for example, 200° C.) for a predetermined time by feeding hot water to cause efficient hydrothermal decomposition, and suppress excessive decomposition of hot-water solubilized hemicellulose, which becomes a solubilized fraction by hydrothermal decomposition, a range in which the temperature is rapidly dropped from a hydrothermal decomposition temperature (200° C.) to a temperature at which excessive decomposition does not proceed (140° C.) due to cooling 45 by a cooling unit is provided, thereby enabling to considerably suppress excessive decomposition.

As a result, excessive decomposition of hemicellulose, which is a hot-water solubilized component, is suppressed. Accordingly, a decrease in the yield of C5 sugar can be reduced.

As the cooling 45, a direct cooling method for directly feeding a refrigerant (cold water), an indirect cooling method using a cooling jacket or the like can be exemplified.

Figure 9:
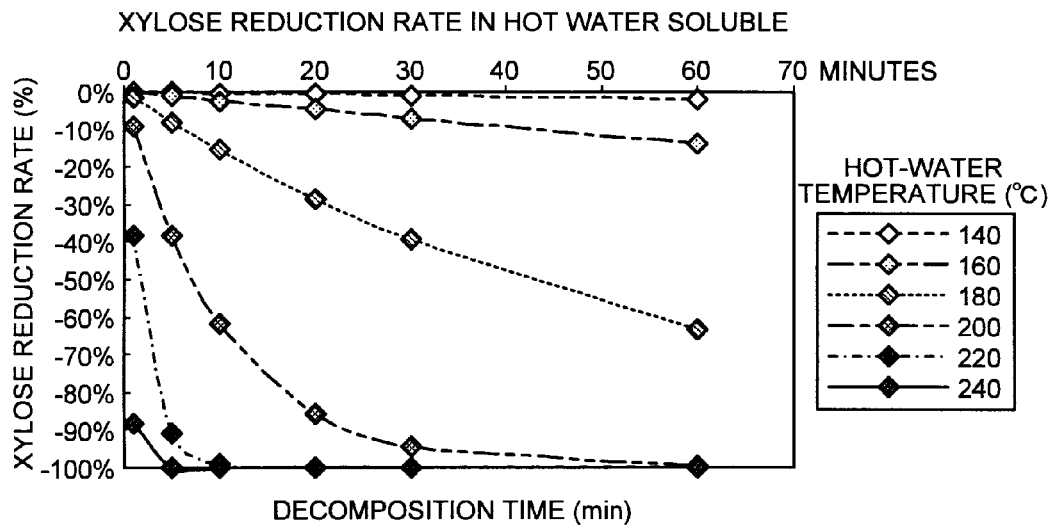
FIG. 9 depicts a relation between a xylose reduction rate in hot water soluble and a decomposition time.
Figure 10:
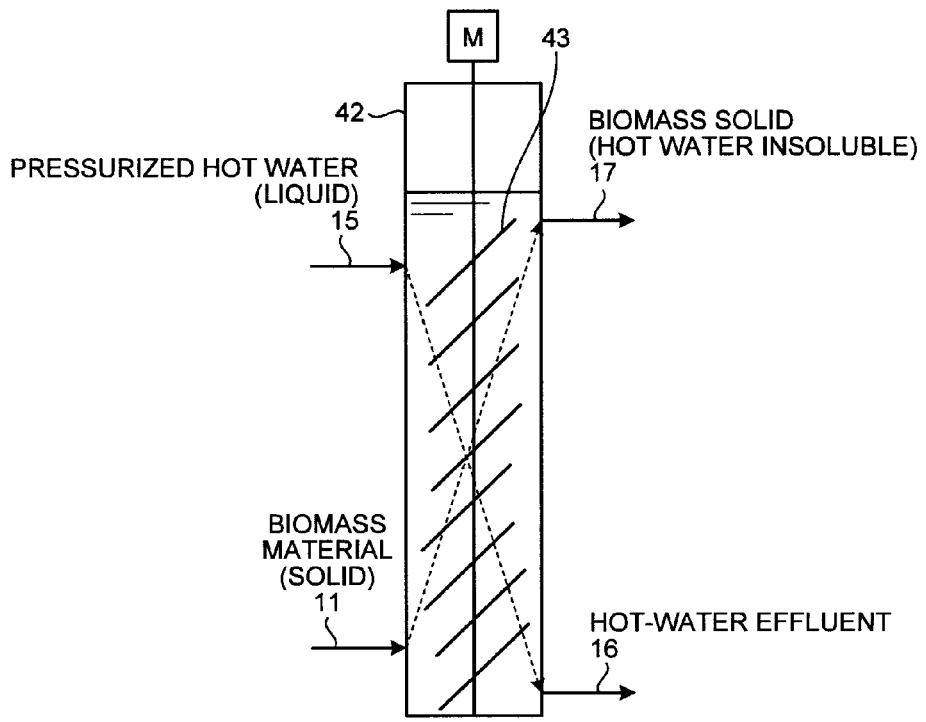
FIG. 10 is a pattern diagram of a vertical apparatus according to a conventional example that hydrothermally decomposes biomass by hot water.
Figure 11:
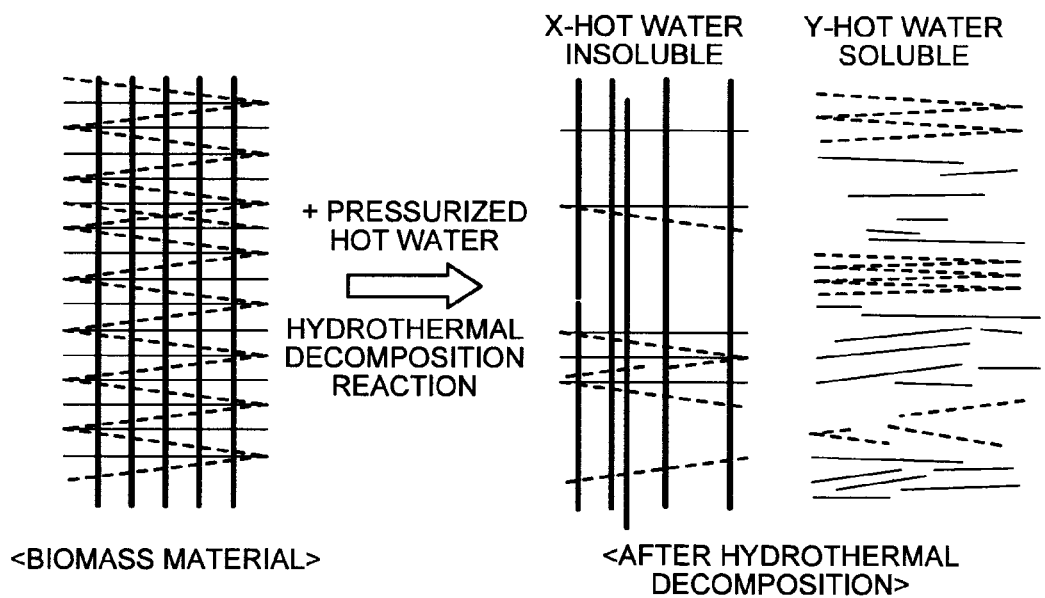
FIG. 11 depicts a decomposition state of biomass by hot water.
Figure 11:
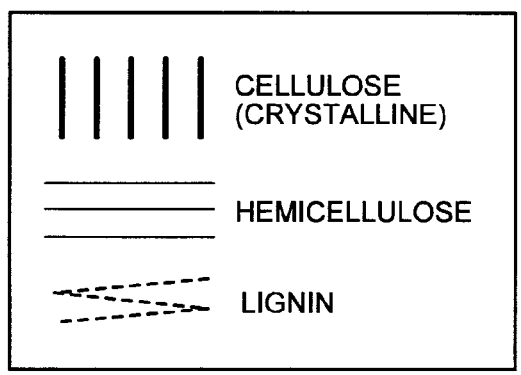

The reason why the temperature is rapidly dropped to 140° C. or less is that the temperature range from 180° C. to 140° C. is a range in which hemicellulose, which is a hot-water solubilized component, is excessively decomposed, as shown in FIG. 9.

In FIG. 9, a decomposition state with a passage of time of hemicellulose solubilized in hot water at each temperature is confirmed by using hot water in which hemicellulose is once dissolved from biomass. Because hemicellulose cannot be directly measured, FIG. 9 depicts a rate of decrease after hemicellulose is converted to C5 sugar (xylose).

As described above, in a state of hot-water solubilized hemicellulose after being solubilized in hot water (in a so-called naked state), because excessive decomposition occurs in a temperature range equal to or higher than 140° C., hemicellulose needs to be cooled quickly down to 140° C. or lower as in the present invention.

If the discharging temperature of the hot-water effluent 16 to be discharged from the apparatus body is made 140° C. or lower by cooling, the hot-water effluent 16 can be immediately discharged. However, for example, the apparatus can have a gradual cooling region C in which the hot-water effluent 16 is gradually cooled to about 100° C. to 120° C., for example, and the hot-water effluent 16 is transferred to the next process.

The reaction time in temperature control of the effective reaction region (the hydrothermal decomposition region) A is preferably 20 minutes or less, and more preferably from 5 to 15 minutes. This is because if reaction is performed for a long time, hemicellulose dissolved in hot water accumulates to increase the rate of the excessive decomposition product, which is not desirable.

As a reaction pressure, it is desired that a pressure higher by 0.1 to 0.5 megapascal is applied to a saturated vapor pressure of water at each temperature of the reaction temperature (180° C. to 240° C.) of the apparatus body 42A.

In this manner, in the present invention, a controller (not shown) performs temperature control such that the temperature is controlled in the effective reaction region (the hydrothermal decomposition region) A, which is a region in which the hemicellulose component is removed from the biomass material 11 by hot water, and the hemicellulose component is rapidly cooled in the temperature drop region (the dissolved-hemicellulose excessive decomposition suppressing region) B in which the hemicellulose component is cooled immediately after it passes the effective reaction region A. Therefore, the solubilized hemicellulose dissolved in hot water is caused to pass through the excessive decomposition temperature region within a time as short as possible, thereby considerably suppressing excessive decomposition of the hemicellulose component, which is a hot-water soluble fraction.

It is desired that the control for changing the temperature from the effective reaction region (the hydrothermal decomposition region) A to the temperature drop region (the dissolved-hemicellulose excessive decomposition suppressing region) B is performed to draw a temperature curve, as shown in the temperature distribution diagram on the right of FIG. 1, such that the temperature changes substantially in a rectangular shape from the linear effective reaction region (the hydrothermal decomposition region) A.

The hot water 15 and the biomass material 11 are brought into counter contact with each other, and the biomass material 11 is washed by the hot water 15 on an upper end side from which the biomass solid 17 is discharged. Even when the excessive decomposition component is present, taking out of the biomass material 11 to outside in the solid state is reduced by the washing effect, thereby purifying the biomass solid 17. Accordingly, a raw material of hexose that hardly causes reaction inhibition can be obtained.

Figure 2:
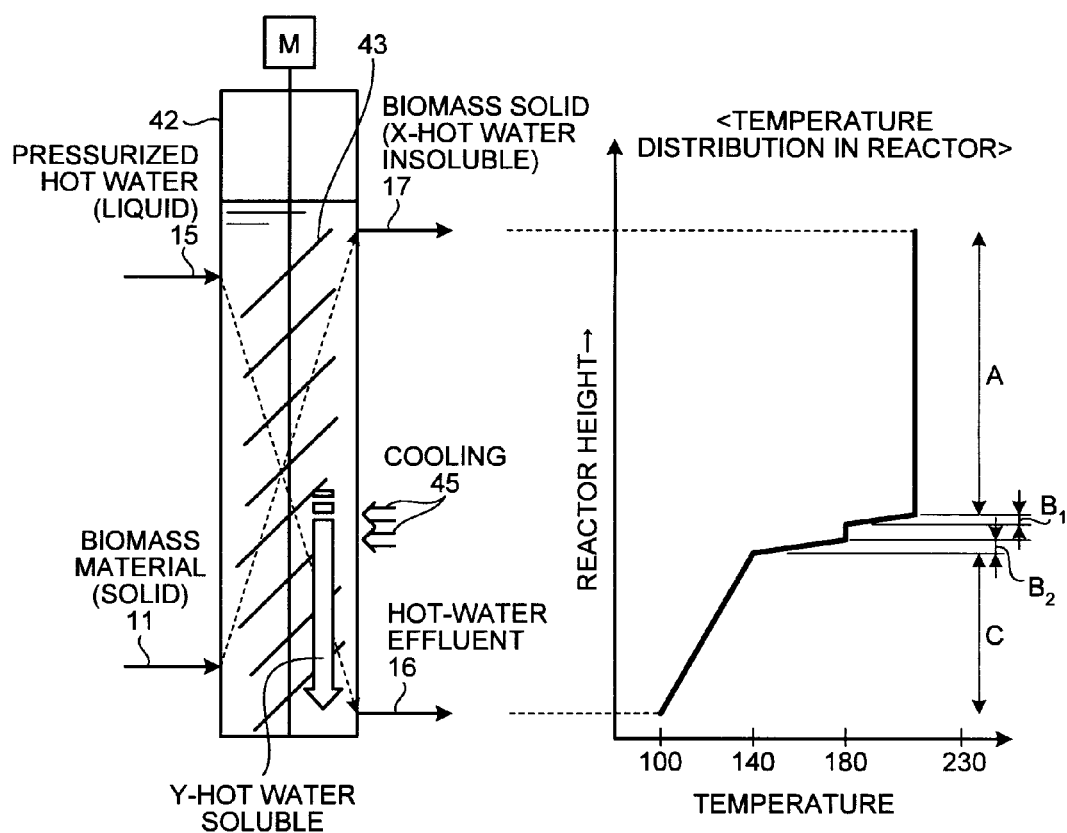
FIG. 2 is a pattern diagram of another hydrothermal decomposition apparatus according to the first embodiment and a temperature distribution.

As shown in FIG. 2, when the temperature of the effective reaction region (the hydrothermal decomposition region) A is 180° C. or higher (for example, 200° C.), this temperature of the effective reaction region is maintained at 200° C. for a predetermined time, and thereafter a first temperature drop region $B_1$ in which the temperature is dropped from 200° C. to 180° C., and a second temperature drop region $B_2$ in which the temperature is cooled to a temperature at which excessive decomposition does not occur (the temperature is dropped from 180° C. to 140° C.) immediately thereafter can be provided.

This is because, for example, when the hemicellulose component is saccharified to pentose, a different type of sugar such as arabinose and xylose may dissolve at a temperature lower than 200° C. Accordingly, hemicellulose components changing to arabinose dissolve at a low temperature (180° C.). Therefore, it is possible to have a configuration such that these components are dissolved first at a temperature around 180° C., and then hemicellulose components changing to xylose are dissolved at a higher temperature (200° C.).

Hemicellulose dissolved in the hot water passes the temperature drop region (the dissolved-hemicellulose excessive decomposition region) B in which the hot water flows downward immediately after dissolution within a short time, thereby decreasing excessive decomposition.

Figure 3:
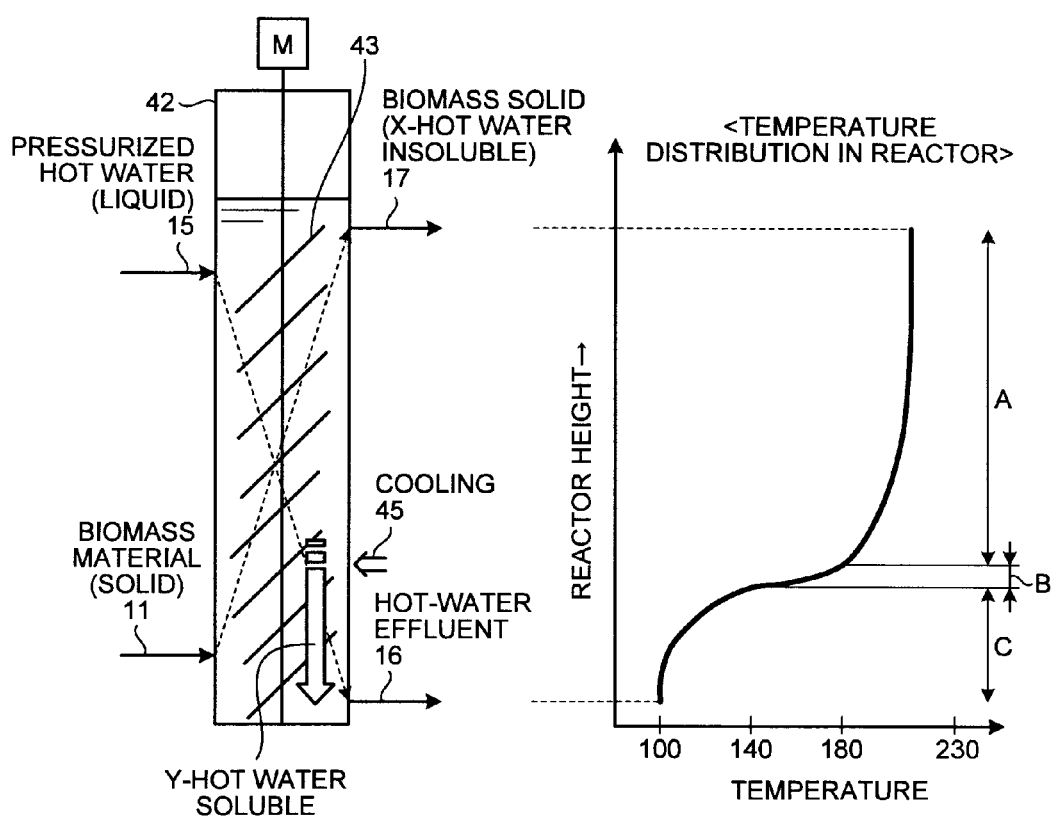
FIG. 3 is a pattern diagram of another hydrothermal decomposition apparatus according to the first embodiment and a temperature distribution.

As shown in FIG. 3, temperature control can be performed such that the feeding temperature (200° C.) of the hot water is maintained for a predetermined time, and thereafter in the temperature drop region B, the temperature is dropped to 180° C. in a gentle curve, and immediately thereafter, the temperature is cooled to a temperature at which excessive decomposition does not occur (the temperature is dropped from 180° C. to 140° C.).

Second Embodiment

A specific example of the biomass hydrothermal decomposition apparatus according to the present invention is explained with reference to the drawings.

Figure 4:
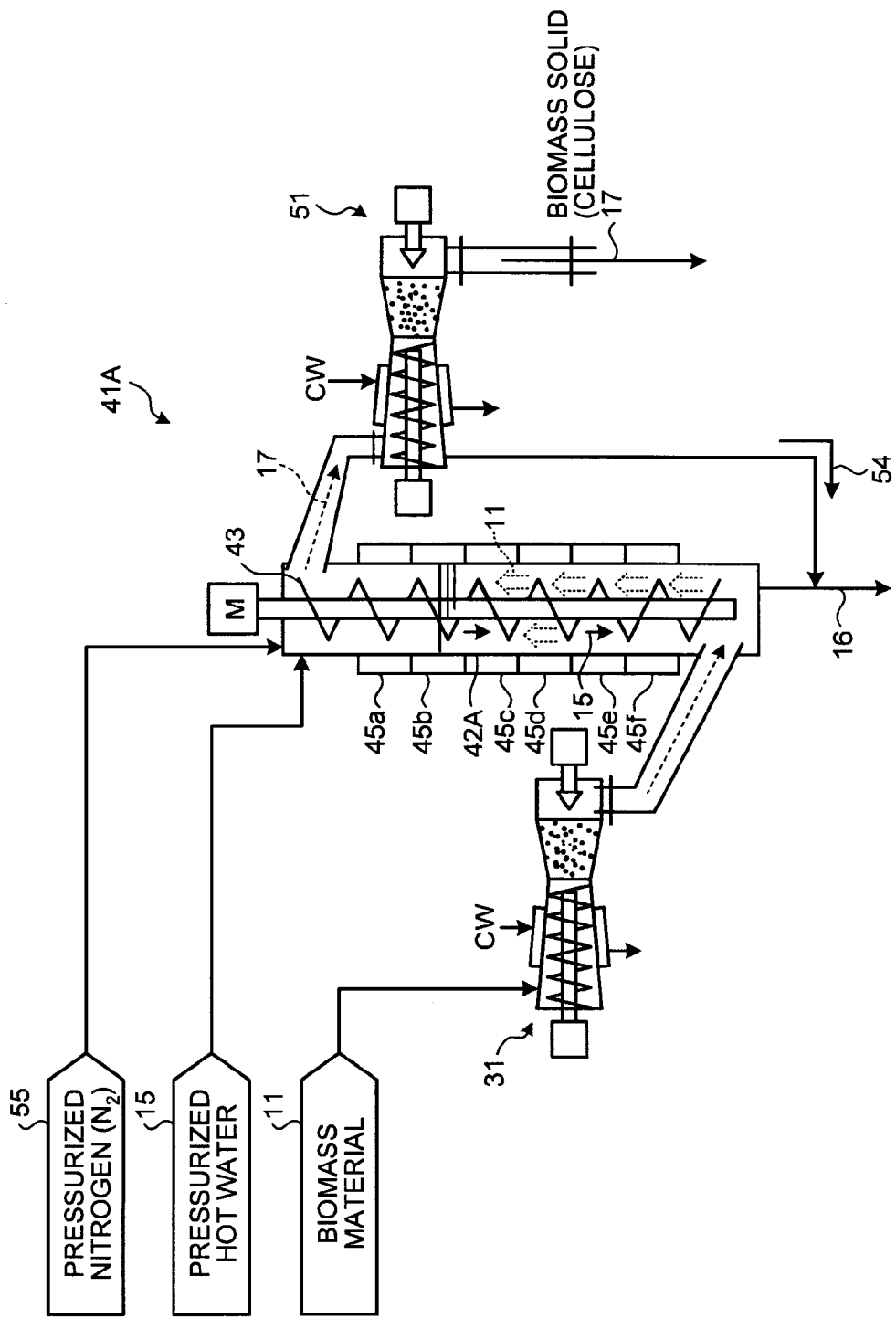
FIG. 4 is a schematic diagram of a hydrothermal decomposition apparatus according to a second embodiment of the present invention.

FIG. 4 is a schematic diagram of a biomass hydrothermal decomposition apparatus according to a second embodiment.

As shown in FIG. 4, a hydrothermal decomposition apparatus 41A according to the present embodiment includes: a biomass feeding device 31 that feeds the biomass material 11 under a normal pressure to under an increased pressure; and the hydrothermal decomposition apparatus 41A that gradually transports the fed biomass material 11 (in the present embodiment, for example, wheat straw) from a lower end side into the vertical apparatus body (hereinafter, "apparatus body") 42A by the transfer screw 43, feeds the hot water 15 from an upper end side different from a feed position of the biomass material 11 into the apparatus body 42A, hydrothermally decomposes the biomass material 11 while bringing the biomass material 11 into counter contact with the hot water 15, and transfers a lignin component and a hemicellulose component into the hot water 15 to separate the lignin component and the hemicellulose component from the biomass material 11. The hydrothermal decomposition apparatus 41A also includes a biomass discharging device 51 that discharges the biomass solid 17 from the upper end side of the apparatus body 42A under an increased pressure to under a normal pressure. In FIG. 4, reference numeral 54 denotes dehydration liquid and reference numeral 55 denotes pressurized nitrogen.

By using the hydrothermal decomposition apparatus 41A, the biomass material 11 and the hot water 15 are brought into counter contact with each other in the apparatus. As a result, the biomass solid 17 mainly including cellulose can be obtained, by transferring a side reaction product (lignin component and hemicellulose component) other than the hydrothermal reaction for generating cellulose (which becomes hexose solution by enzymatic saccharification), which is a target component, into the hot water 15.

At this time, a temperature jacket, which is a temperature adjusting apparatus of the apparatus body 41A, is divided into a plurality of elements 45a to 45f constituted by heating-medium feeding units 45a to 45d and cooling-medium feeding units 45e to 45f.

Temperature control for maintaining a predetermined temperature (for example, 200° C.) with the hot water 15 being fed is then performed by feeding a heating medium at a predetermined temperature in the heating-medium feeding units 45a to 45d, thereby efficiently effecting hydrothermal decomposition.

Thereafter, temperature control is performed to drop the temperature quickly from the hydrothermal decomposition temperature (200° C.) to a temperature (140° C.) at which excessive decomposition does not proceed, by feeding a cooling medium at a predetermined temperature in the cooling-medium feeding units 45e to 45f, in order to suppress excessive decomposition of the hydrothermally solubilized hemicellulose, which has become solubilized fractions due to the cooling medium. Therefore, excessive decomposition of hemicellulose, which is a hydrothermally solubilized component, is suppressed. Accordingly, a decrease in the yield of C5 sugar is reduced.

As a result, with the biomass solid 17, cellulose can be efficiently saccharified to a first sugar solution containing hexose, thereby enabling to efficiently produce various organic materials (for example, alcohol) from the sugar solution.

On the other hand, the hemicellulose component in the hot-water effluent 16 discharged from the hydrothermal decomposition apparatus 41A can be saccharified to a second sugar solution containing pentose, thereby enabling to efficiently produce various organic materials (for example, alcohol) from the sugar solution.

In the present embodiment, while the biomass material 11 is fed from the lower end side, the present invention is not limited thereto. Conversely, the biomass material 11 can be fed from the upper end side. At this time, the hot water 15 is fed from the lower end side.

The biomass feeding device 31 that feeds the biomass under a normal pressure to under an increased pressure includes a pump unit such as a piston pump or a slurry pump.

In the present embodiment, the hydrothermal decomposition apparatus 41A is a vertical apparatus as shown in FIG. 4. However, the present invention is not limited thereto, and a gradient-type or horizontal-type hydrothermal decomposition apparatus can be used.

The reason why the hydrothermal decomposition apparatus is the gradient type or vertical type is that gas generated in the hydrothermal decomposition reaction and gas brought into a raw material can quickly escape from above, which is preferable. Further, because the decomposition product is extracted by the hot water 15, concentration of the extracted product increases from the upper side toward the lower side, which is preferable in view of the extraction efficiency.

In the hydrothermal decomposition apparatus 41A according to the present embodiment, by providing the transfer screw 43, (1) the solid can be transported in a solid-liquid counter flow; (2) solid liquid separation becomes possible in the apparatus body 42A; and (3) mixture of the hot water 15 on the surface of the solid and inside the solid is progressed in the apparatus body 42A to facilitate reaction.

Further, a scraper (not shown) that prevents clogging of an discharging hole of the hot-water effluent 16 can be provided in the transfer screw 43.

In the present embodiment, a temperature jacket has been explained as an example of the temperature adjusting apparatus. However, the present invention is not limited thereto, and for example, a method of injecting cold water or a temperature adjusting method by external heat exchange can be appropriately used.

Third Embodiment

Another embodiment of the biomass hydrothermal decomposition apparatus according to the present invention is explained with reference to the drawings.

Figure 5:
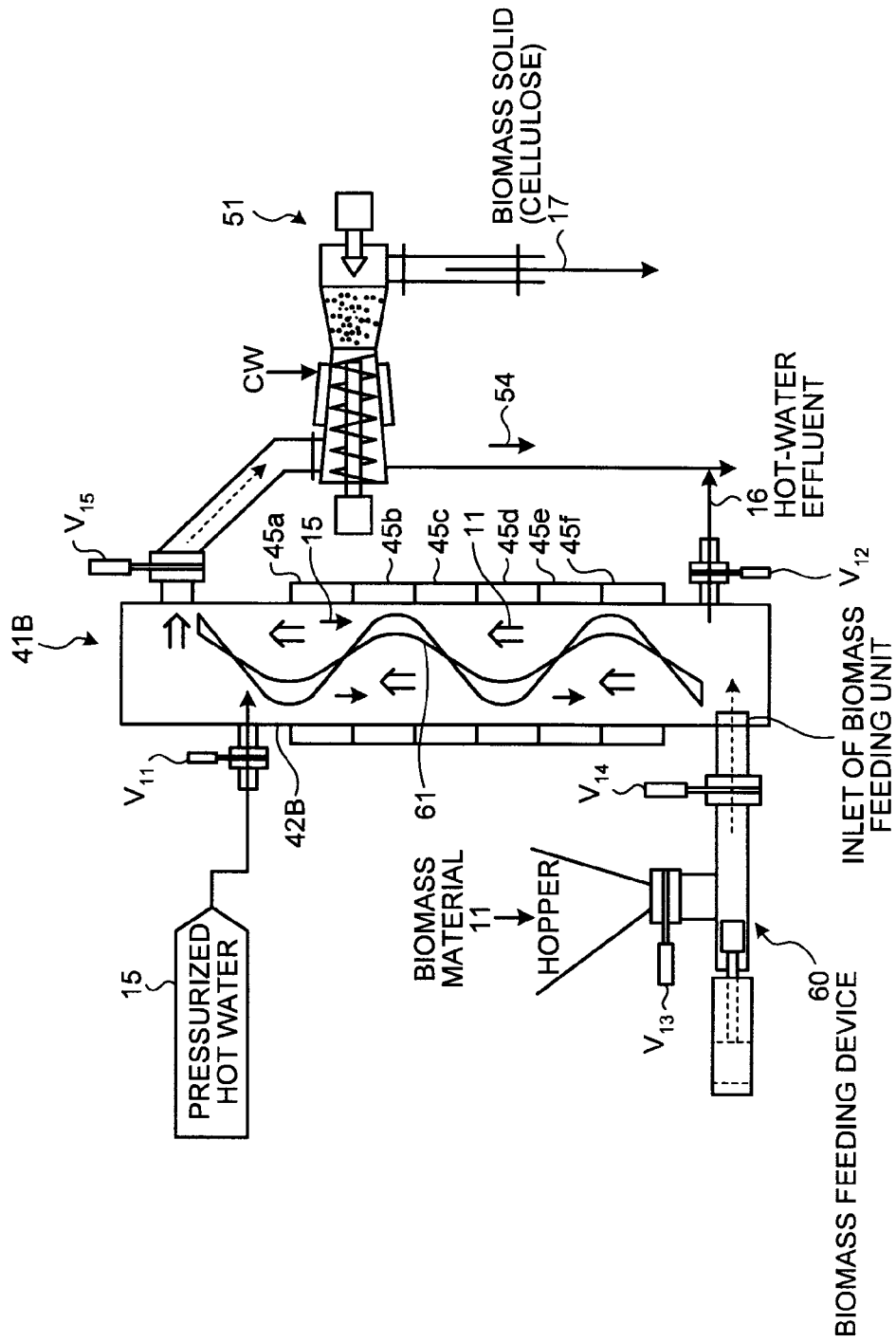
FIG. 5 is a schematic diagram of another biomass hydrothermal decomposition apparatus according to a third embodiment of the present invention.

FIG. 5 is a schematic diagram of another biomass hydrothermal decomposition apparatus according to a third embodiment.

As shown in FIG. 5, a biomass hydrothermal decomposition apparatus 41B according to the present embodiment includes: a biomass feeding device 60 that feeds the biomass material 11 (for example, wheat straw) under a normal pressure to under an increased pressure; and the hydrothermal decomposition apparatus 41B that gradually moves the fed biomass material 11 from either end side of upper and lower ends (in the present embodiment, the lower end side) in a vertical apparatus body (hereinafter, "apparatus body") 42B in a consolidated state, feeds the hot water 15 from an end (in the present embodiment, the upper end side) different from a feed position of the biomass material 11 into the apparatus body 42B, hydrothermally decomposes the biomass material 11 while bringing the biomass material 11 into counter contact with the hot water 15, and transfers a lignin component and a hemicellulose component into the hot water 15 to separate the lignin component and the hemicellulose component from the biomass material 11. The hydrothermal decomposition apparatus 41B also includes the biomass discharging device 51 that discharges the biomass solid 17 from the feed position side of the hot water 15 of the apparatus body 42B under an increased pressure to under a normal pressure. Reference signs $V_{11}$ to $V_{15}$ denote ON-OFF valves.

The biomass feeding device 60 that feeds the biomass under a normal pressure to under an increased pressure includes a pump unit such as a piston pump or a slurry pump.

In the present embodiment, inside the apparatus body 42B, there is provided a fixed stirring unit 61 that stirs the biomass material 11 in a consolidated state, in a so-called plug flow, so that the biomass material 11 to be fed therein is stirred by a stirring function, when moved axially.

By providing the fixed stirring unit 61, mixture of the hot water 15 on the surface of the solid and inside the solid is progressed in the apparatus body 42B to promote reaction.

In the present invention, as for the flow of the hot water 15 and the biomass material 11 in the apparatus body 42B of the hydrothermal decomposition apparatus 41B, it is desired that the biomass material 11 and the hot water 15 are stirred and caused to flow in a so-called counter flow in which the biomass material 11 and the hot water 15 are brought into counter contact with each other.

The hydrothermal decomposition apparatus 41B performs hydrothermal decomposition in a plug flow. Therefore, its configuration is simple, and the solid biomass material 11 moves parallel to a central axis of a pipe, while being stirred vertically to the central axis of the pipe. Meanwhile, the hot water 15 (hot water, liquid dissolving decomposed products) moves while being soaked between solid particles by a counter flow against the solid.

Further, in the plug flow, a uniform flow of the hot water 15 can be realized. It is because when the solid biomass material 11 is decomposed by the hot water 15, the decomposed product dissolves on the hot water side, and thus the viscosity around a decomposed portion increases, so that hot water moves preferentially to around an undecomposed portion, then causing decomposition of the undecomposed portion. This configuration creates a uniform flow of hot water, thereby realizing uniform decomposition.

In the apparatus body 42B, due to the resistance of an inner pipe wall of the apparatus body 42B in the hydrothermal decomposition apparatus 41B, the solid density on the outlet side of the biomass material 11 is reduced as compared with that on the inlet side of the biomass material 11. In addition, the amount of the biomass solid 17 decreases due to the decomposition, to increase the ratio of the hot water 15. Consequently, the liquid retention time increases, causing excessive decomposition of decomposed components in the liquid. Therefore, at least the fixed stirring unit 61 is provided.

At this time, a temperature jacket, which is a temperature adjusting apparatus of the apparatus body 41A, is divided into a plurality of the elements 45a to 45f constituted by the heating-medium feeding units 45a to 45d and the cooling-medium feeding units 45e to 45f.

Temperature control for maintaining a predetermined temperature (for example, 200° C.) with the hot water 15 being fed is then performed by feeding a heating medium at a predetermined temperature in the heating-medium feeding units 45a to 45d, thereby efficiently effecting hydrothermal decomposition.

Thereafter, temperature control is performed to drop the temperature quickly from the hydrothermal decomposition temperature (200° C.) to a temperature (140° C.) at which excessive decomposition does not proceed, by feeding a cooling medium at a predetermined temperature in the cooling-medium feeding units 45e to 45f, in order to suppress excessive decomposition of the hydrothermally solubilized hemicellulose, which has become solubilized fractions due to the cooling medium. Therefore, excessive decomposition of hemicellulose, which is a hydrothermally solubilized component, is suppressed. Accordingly, a decrease in the yield of C5 sugar is reduced.

In the present embodiment, a temperature jacket has been explained as an example of the temperature adjusting apparatus. However, the present invention is not limited thereto, and for example, a method of injecting cold water or a temperature adjusting method by external heat exchange can be appropriately used.

Fourth Embodiment

A production system of alcohol, which is an organic material, using a biomass material according to a fourth embodiment of the present invention is explained with reference to the drawings.

Figure 6:
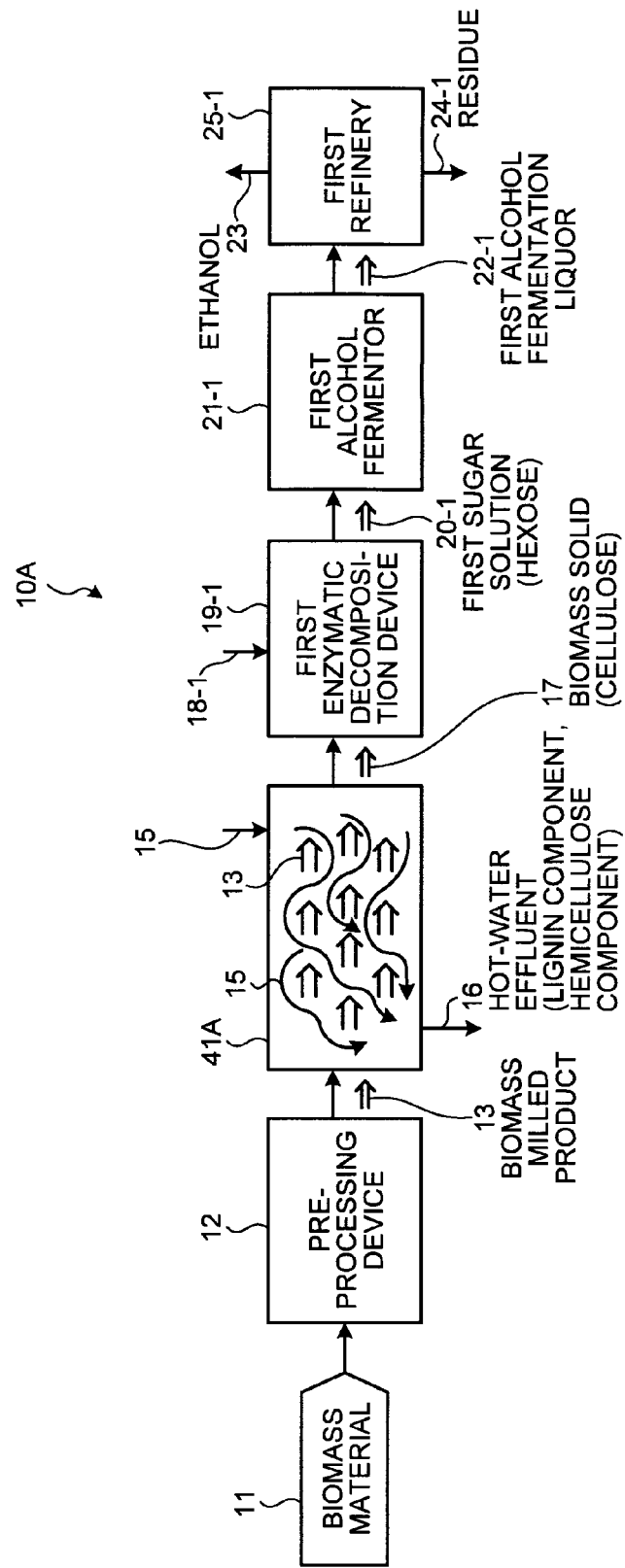
FIG. 6 is a schematic diagram of a production system of alcohol as an organic material using a biomass material according to a fourth embodiment of the present invention.

FIG. 6 is a conceptual diagram of a production system of an organic material using the biomass material according to the present embodiment.

As shown in FIG. 6, an alcohol production system 10A using the biomass material according to the present embodiment includes a pre-processing device 12 that performs, for example, milling of the biomass material 11, the hydrothermal decomposition apparatus 41A shown in FIG. 4 that performs hydrothermal decomposition of the biomass material, while bringing a preprocessed biomass milled product 13 into counter contact with the hot water 15, to transfer the lignin component and the hemicellulose component into the hot water 15, thereby separating the lignin component and the hemicellulose component from a biomass solid, a first enzymatic decomposition device 19-1 that processes cellulose in the biomass solid 17 discharged from the hydrothermal decomposition apparatus 41A with enzyme to decompose cellulose into a sugar solution containing hexose by a first enzyme (cellulase) 18-1, a first alcohol fermentor 21-1 that produces alcohol (ethanol in the present embodiment) by fermentative treatment by using a first sugar solution (hexose) 20-1 obtained by the first enzymatic decomposition device 19-1, and a first refinery 25-1 that refines a first alcohol fermentation liquor 22-1 to separate the first alcohol fermentation liquor 22-1 into ethanol 23, which is a desired product, and a residue 24-1.

According to the present invention, in the biomass hydrothermal decomposition apparatus 41A as shown in FIG. 4, the lignin component and the hemicellulose component are transferred into the hot water 15 on the liquid side by adopting counter flow, so that cellulose remains in the biomass solid 17 on the solid side, thereby acquiring the first sugar solution (hexose) 20-1 by the first enzymatic decomposition device 19-1 for enzymic saccharification.

Accordingly, a fermenting process according to hexose (fermentation according to an end product: in the present embodiment, the ethanol 23 is obtained due to fermentation by using the first alcohol fermentor 21-1) can be established.

In the present embodiment, ethanol of alcohol is exemplified as the product to be obtained by the fermentative treatment. However, the present invention is not limited thereto, and petroleum substitutes, which become chemical product raw materials, or amino acid, which becomes a food/feed material other than alcohol can be obtained by the fermentor.

Various materials such as LPG, automotive fuel, aircraft jet fuel, kerosene petroleum, diesel oil, various heavy oils, fuel gas, naphtha, ethylene glycol as naphtha decomposition product, ethanol amine, alcohol ethoxylate, vinyl chloride polymer, alkyl aluminum, PVA, vinyl acetate emulsion, polystyrene, polyethylene, polypropylene, polycarbonate, MMA resin, nylon, and polyester can be efficiently produced as a chemical product from a sugar solution. Therefore, the sugar solution derived from biomass can be efficiently used as substitutes of chemical products derived from crude oil, which is a depleting fuel, and as a raw material for producing the substitutes.

Fifth Embodiment

A production system of alcohol, which is an organic material, using a biomass material according to a fifth embodiment of the present invention is explained with reference to the drawings.

Figure 7:
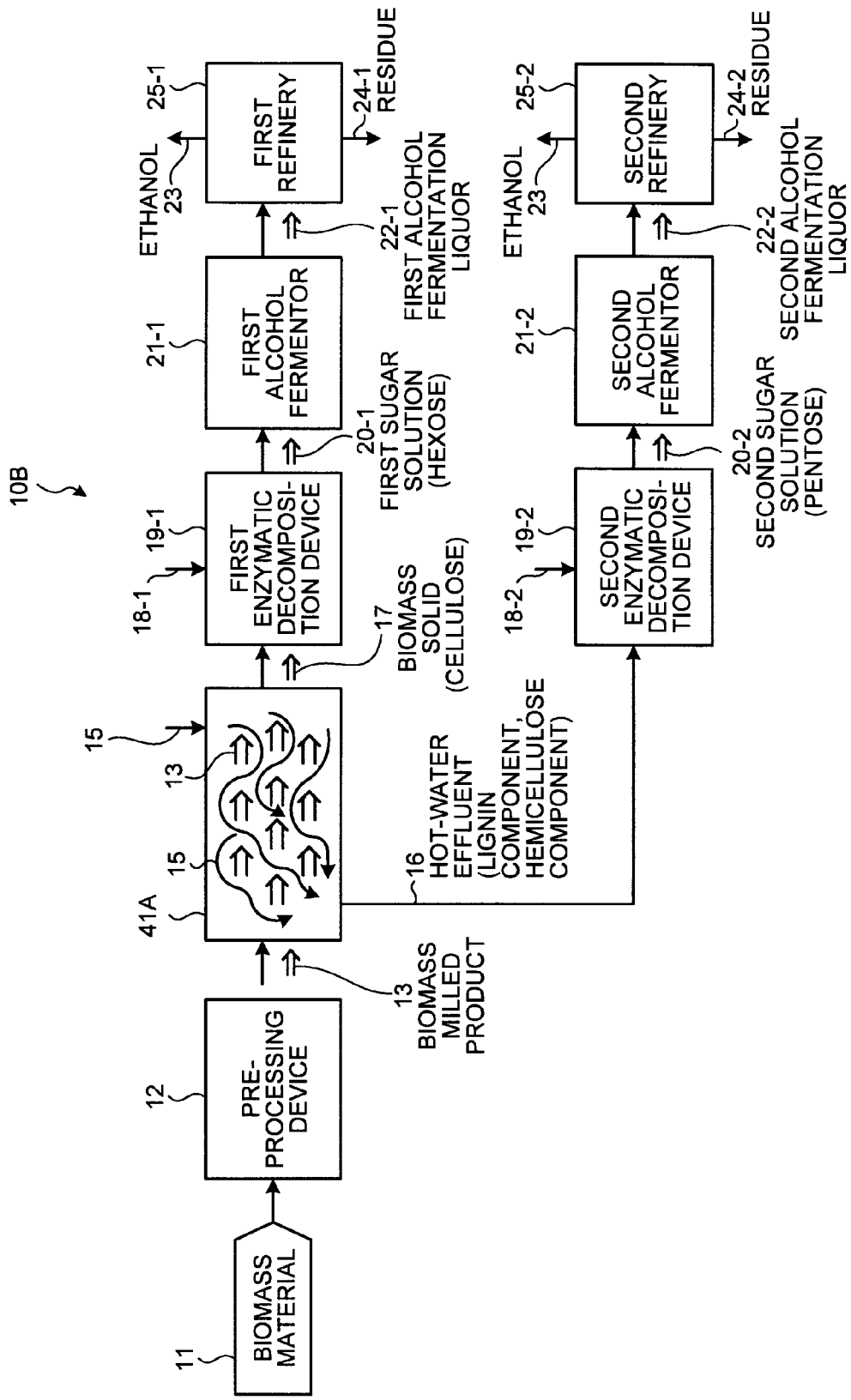
FIG. 7 is a schematic diagram of a production system of alcohol as an organic material using a biomass material according to a fifth embodiment of the present invention.

FIG. 7 is a conceptual diagram of a production system of alcohol, which is an organic material, using the biomass material according to the present embodiment.

As shown in FIG. 7, an alcohol production system 10B using the biomass material according to the present embodiment includes a second enzymatic decomposition device 19-2 that processes a hemicellulose component transferred into the hot-water effluent 16 discharged from the hydrothermal decomposition apparatus 41A with enzyme, to decompose the hemicellulose component into a second sugar solution 20-2 containing pentose, in the alcohol production system 10A shown in FIG. 6.

Two enzymatic decomposition devices, two alcohol fermentors, and two refineries (a first enzymatic decomposition device 19-1 and a second enzymatic decomposition device 19-2, a first alcohol fermentor 21-1 and a second alcohol fermentor 21-2, and a first refinery 25-1 and a second refinery 25-2) are provided separately. The ethanol 23 is obtained by performing an enzymatic decomposition process, an alcohol fermentation process, and a refining process according to the first sugar solution (hexose) 20-1 and the second sugar solution (pentose) 20-2.

In the present embodiment, after a second alcohol fermentation liquor 22-2 is obtained by the fermentation process performed by the second alcohol fermentor 21-2 by using the second sugar solution (pentose) 20-2 obtained by the second enzymatic decomposition device 19-2 using the second enzyme 18-2, the ethanol 23 can be produced by the second refinery 25-2. Reference numeral 24-2 denotes a residue.

Hot-water effluent is not always processed in separate systems, and various changes can be made such that, for example, a process after the enzymatic decomposition device is communalized, a process after the alcohol fermentor is communalized, or a process after the refinery is communalized.

Figure 8:
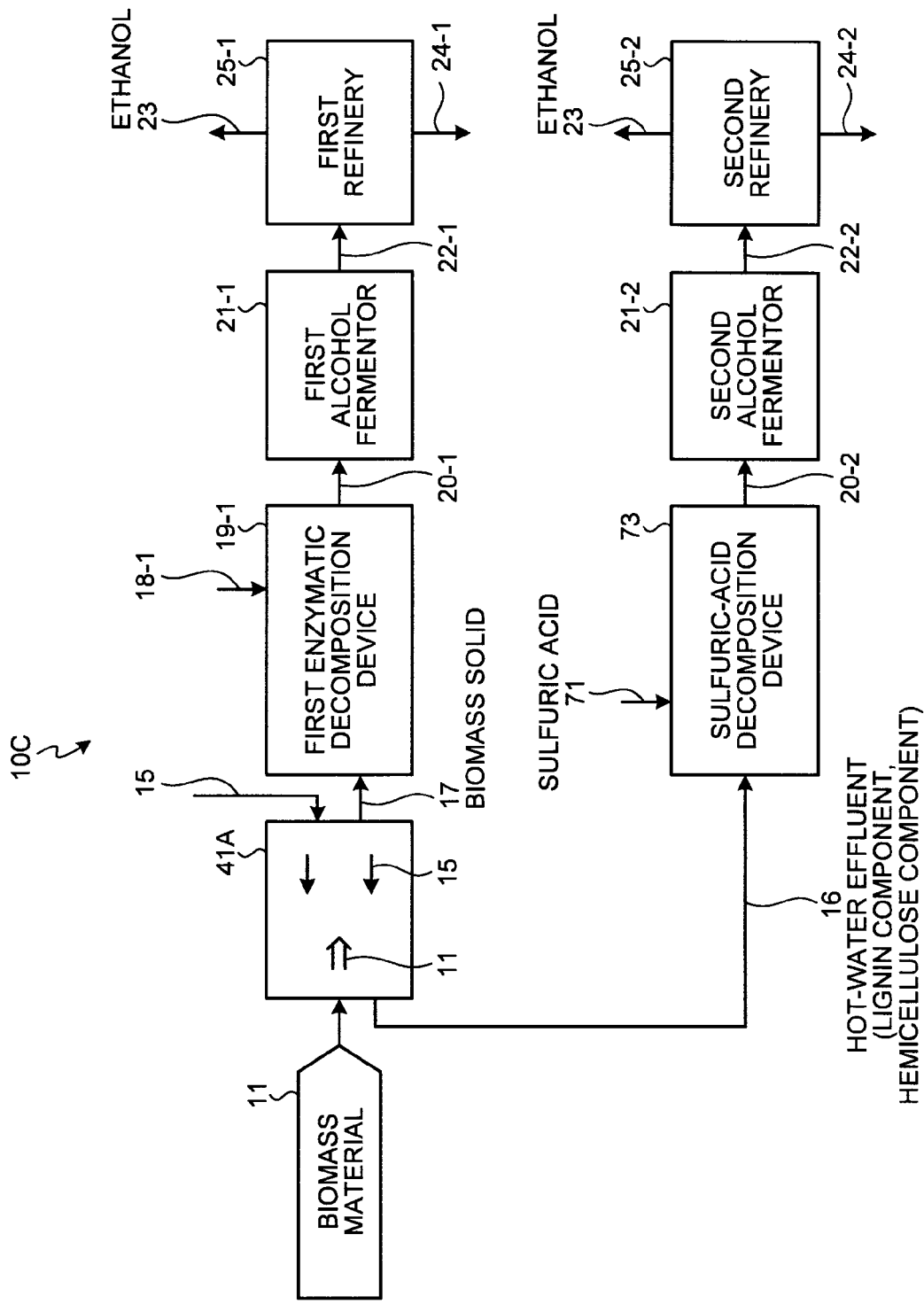
FIG. 8 is a schematic diagram of another production system of alcohol as an organic material using a biomass material according to the fifth embodiment.

FIG. 8 is a conceptual diagram of a production system of alcohol, which is an organic material using a biomass material according to a modification of the present embodiment.

As shown in FIG. 8, in the alcohol production system 10A shown in FIG. 6, an alcohol production system 10C according to the present embodiment includes a sulfuric-acid decomposition device 73 that discharges the hot water 15, into which the lignin component and the hemicellulose component are transferred, to outside as the hot-water effluent 16, feeds sulfuric acid 71 to the hot-water effluent 16, and decomposes the hemicellulose component in the hot-water effluent 16 with sulfuric acid to decompose the hemicellulose component into the second sugar solution 20-2 containing pentose, the second alcohol fermentor 21-2 that produces alcohol (ethanol in the present embodiment) by the fermentative treatment by using the obtained second sugar solution (pentose) 20-2, and the second refinery 25-2 that refines the second alcohol fermentation liquor 22-2 to separate the second alcohol fermentation liquor 22-2 into the ethanol 23, which is a desired product, and a second residue 24-2.

In the present embodiment, the ethanol 23 can be produced by the fermentative treatment by using the second sugar solution (pentose) 20-2 obtained by the sulfuric-acid decomposition device 73.

Decomposition conditions for the sulfuric-acid decomposition device in the present invention are such that concentration of sulfuric acid is 0.1% to 5% by weight, preferably, 1% to 4% by weight, decomposition temperature is 100° C. to 140° C., preferably about 120° C., and a decomposition time is for 30 minutes to 3 hours, preferably, about 1 hour. This is because, if the decomposition conditions are outside these ranges, favorable decomposition of hemicellulose cannot be realized.

Conventionally, when the biomass material is directly decomposed with sulfuric acid, the decomposition process is performed at a temperature as high as about 180° C. for about 10 minutes, by using 1% by weight of sulfuric acid. However, because sulfuric acid acts as an inhibitor at the time of enzymic saccharification of cellulose on a downstream side, the yield of hexose decreases.

On the other hand, in the present invention, in the biomass hydrothermal decomposition apparatus 41A, the cellulose component is caused to remain in the biomass solid 17 beforehand, to process the hot-water effluent 16 containing the hemicellulose component transferred to the hot water 13 side with sulfuric acid under a low-temperature condition. Therefore, the structure of sulfuric acid facilities can be simplified, and a usage amount of sulfuric acid can be considerably suppressed (to 0.6 to 0.9 times the conventional usage amount of sulfuric acid). As a result, the amount of disposal (gypsum treatment) of sulfuric acid is reduced, thereby enabling to reduce the facility size for recovering and separating sulfuric acid and downsize the facilities.

Because decomposition using sulfuric acid can be performed at a temperature as low as 140° C. or lower, any conventional heat-resistant facilities for high temperature (180° C.) is not required, thereby enabling to reduce the cost of the facilities.

According to the present invention, in the biomass hydrothermal decomposition apparatus 41A (41B), by adopting counter flow, cellulose remains in the biomass solid 17 on the solid side, and the first enzymatic decomposition device 19-1 for enzymic saccharification obtains the first sugar solution (hexose) 20-1, and in the hot water 15 on the liquid side, the hemicellulose component dissolved in the hot water 15 is separated as the hot-water effluent 16. The second enzymatic decomposition device 19-2 for enzymic saccharification or the sulfuric-acid decomposition device 73 obtains the second sugar solution (pentose) 20-2 separately. Therefore, the both sugar solutions can be efficiently separated and saccharized, respectively. The fermentation process according to hexose and pentose (fermentation according to the end product: for example, ethanol fermentation) can be established.

As described above, by adopting counter flow in the biomass hydrothermal decomposition apparatus 41A, a side reaction product, which becomes an inhibitor in the enzymic saccharification reaction for obtaining hexose, and the lignin component soluble in hot water are transferred to the hot water 15 side. Therefore, the cellulose-based biomass solid 17 can be obtained, thereby improving the saccharification yield of hexose in the saccharification reaction thereafter.

On the other hand, the hemicellulose component contained in the separated hot-water effluent 16 is saccharized in the second enzymatic decomposition device 19-2, thereby enabling to obtain the sugar solution containing pentose.

By using a fermentum or the like suitable for hexose and pentose, respectively, the ethanol 23 can be efficiently and individually obtained by fermentation.

Further, at the time of the hydrothermal reaction, in the reaction apparatus, there are provided the effective reaction region (the hydrothermal decomposition region) A formed from the other side to the one side of the apparatus body 42, in which the feeding temperature of the hot water 15 (180 to 240° C., such as 200° C.) is maintained for a certain period of time to cause hydrothermal decomposition, and the temperature drop region (the dissolved-hemicellulose excessive decomposition suppressing region) B in which the temperature is rapidly dropped (for example, from 200° C. to 140° C.) to a temperature (for example, 140° C.) at which the hot-water soluble fractions are not excessively decomposed, immediately after it is out of the effective reaction region A. As a result, excessive decomposition of hemicellulose is suppressed, and thus a decrease in the yield of C5 sugar can be suppressed.

As described above, according to the present invention, a production system of an organic material using a biomass material that separates cellulose-based component and hemicellulose component transferred to hot water, suppresses excessive decomposition of hemicellulose, to enable efficient production of the sugar solutions (a hexose solution and a pentose solution) suitable for respective components, and can efficiently produce various organic materials (for example, alcohol, petroleum substitutes, or amino acid) from the sugar solution can be provided.

INDUSTRIAL APPLICABILITY

As described above, the hydrothermal decomposition apparatus according to the present invention separates a component mainly including cellulose from a biomass material and efficiently produces a sugar solution. Further, various organic materials (for example, alcohol, petroleum substitutes, or amino acid) can be efficiently produced from the sugar solution.

REFERENCE SIGNS LIST 11 biomass material
12 pre-processing device
13 biomass milled product
15 hot water
16 hot-water effluent
17 biomass solid
18 enzyme
19-1 first enzymatic decomposition device
19-2 second enzymatic decomposition device
20-1 first sugar solution (hexose)
20-2 second sugar solution (pentose)
23 ethanol
41A, 41B hydrothermal decomposition apparatus
42 apparatus body
43 transfer screw

The invention claimed is:

1. A temperature control method of a biomass hydrothermal decomposition apparatus, the method comprising:
   using a biomass hydrothermal decomposition apparatus that feeds a solid biomass material including cellulose, hemicellulose and lignin from one side of an apparatus body;
   feeding pressurized hot water from the other side of the apparatus body, to hydrothermally decompose the biomass material while bringing the biomass material into counter contact with the pressurized hot water;
   dissolving hot-water soluble fractions in the pressurized hot water;
   discharging the pressurized hot water to outside from the one side of the apparatus body;
   discharging the biomass material to outside from the other side of the apparatus body;
   preparing a temperature adjusting apparatus provided between the other side and the one side of the apparatus body, the temperature adjusting apparatus including:
   a plurality of heating-medium feeding units for maintaining a feeding temperature of the pressurized hot water and
   a plurality of cooling-medium feeding units provided downstream of the plurality of heating-medium feeding units, for cooling the temperature of the pressurized hot water:
   maintaining the feeding temperature of the pressurized hot water with the plurality of heating-medium feeding units and providing an effective reaction region where the feeding temperature of the pressurized hot water is maintained, so as to hydrothermally decompose the biomass material in the effective reaction region and dissolve hemicellulose and lignin components into the pressurized hot water; and
   cooling the pressurized hot water with the plurality of cooling-medium feeding units so as to provide at least two regions,
   wherein at the cooling the pressurized hot water,
   a first temperature drop region of the at least two regions, where a temperature of the pressurized hot water is lower than that of the effective reaction region, is provided downstream of the effective reaction region, and
   a second temperature drop region of the at least two regions, where a temperature of the pressurized hot water is lower than that of the first temperature drop region, is provided downstream of first temperature drop region,
   wherein in the first temperature drop region, dissolving of a hemicellulose component which changes to a sugar is suppressed,
   wherein in the second temperature drop region, dissolving of the hemicellulose component is further suppressed,
   wherein
   the feeding temperature of the pressurized hot water is a predetermined temperature that is higher than 180° C. and equal to or lower than 240° C.,
   the first temperature drop region is a temperature range that is lower than the feeding temperature and equal to or higher than 180° C., and
   the second temperature drop region is a temperature range that is lower than 180° C. and equal to or higher than 140° C.

* * * * *